United States Patent
Ito et al.

(10) Patent No.: US 6,525,058 B1
(45) Date of Patent: Feb. 25, 2003

(54) PHARMACEUTICAL COMPOSITION FOR ORAL USE

(75) Inventors: Akira Ito, Shizuoka (JP); Hiroshi Sugiura, Shizuoka (JP); Shigeru Yamazaki, Shizuoka (JP)

(73) Assignees: Yamanouchi Pharmaceutical Co., LTD, Tokyo (JP); Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 10/009,797

(22) PCT Filed: Jun. 16, 2000

(86) PCT No.: PCT/JP00/03940

§ 371 (c)(1),
(2), (4) Date: Dec. 13, 2001

(87) PCT Pub. No.: WO00/78318

PCT Pub. Date: Dec. 28, 2000

(30) Foreign Application Priority Data

Jun. 18, 1999 (JP) .............................. 11-172237

(51) Int. Cl.[7] .......................................... A61K 31/497
(52) U.S. Cl. .................................................. 514/254.02
(58) Field of Search ..................................... 514/254.02

(56) References Cited

U.S. PATENT DOCUMENTS

| | | | | |
|---|---|---|---|---|
| 5,610,169 A | * | 3/1997 | Iowa et al. | 514/334 |
| 5,972,911 A | * | 10/1999 | Yesair | 514/77 |
| 6,121,234 A | * | 9/2000 | Benet et al. | 514/11 |
| 6,160,007 A | * | 12/2000 | DeMichele et al. | 514/458 |
| 2002/0049213 A1 | * | 4/2002 | Weidner Wells et al. | 514/252.05 |

FOREIGN PATENT DOCUMENTS

EP 741133 A2 11/1996

OTHER PUBLICATIONS

Gante, et al. "New Antithrombotic RGD–mimetics with the high bioavalability", Bioorg. Med. Chem. (1996) 6(20), pp. 2425–30.
International Search Report.

* cited by examiner

*Primary Examiner*—James H Reamer
(74) *Attorney, Agent, or Firm*—Sughrue Mion, PLLC

(57) ABSTRACT

The present invention is to provide a stabilized pharmaceutical composition for oral use containing 1-ethyl methylester 4-[[3-[p-(carboxyamidino)phenyl]-2-oxo-5-oxazolidinyl] methyl]-1-piperazineacetate or a pharmaceutically acceptable salt thereof having an antagonistic action to GPIIb/IIIa receptor and an oily base. The present invention is to further provide a method for the manufacture of a stabilized pharmaceutical composition for oral use by compounding 1-ethyl methylester 4-[[3-[p-(carboxyamidino)phenyl]-2-oxo-5-oxazolidinyl]methyl]-1-piperazineacetate or a pharmaceutically acceptable salt thereof with an oily base. The present invention is to furthermore provide a method for the stabilization of a pharmaceutical composition by compounding 1-ethyl methylester 4-[[3-[p-(carboxyamidino)phenyl]-2-oxo-5-oxazolidinyl]-methyl]-1-piperazineacetate or a pharmaceutically acceptable salt thereof with an oily base.

16 Claims, No Drawings

PHARMACEUTICAL COMPOSITION FOR ORAL USE

TECHNICAL FIELD

The present invention relates to a stable pharmaceutical composition for oral use of 1-ethyl methylester 4-[[3-[p-(carboxyamidino)phenyl]-2-oxo-5-oxazolidinyl]methyl]-1-piperazineacetate or a pharmaceutically acceptable salt thereof and also to a method for manufacturing the composition thereof. The present invention further relates to a method for stabilization of a pharmaceutical composition comprising 1-ethyl methylester 4-[[3-[p-(carboxyamidino)phenyl]-2-oxo-5-oxazolidinyl]methyl]-1-piperazineacetate or a pharmaceutically acceptable salt thereof.

BACKGROUND OF THE INVENTION

In the Japanese Laid-Open Patent Hei-08/301857 (corresponding to the European Patent 741,133), there is a report that a series of amidine derivatives is able to suppress particularly the interaction of integrin receptor with a ligand, to particularly suppress a binding of fibrinogen, fibronectin and a von Willebrand factor with fibrinogen receptor (glycoprotein IIb/IIIa) of platelets, to suppress a binding of adhesion protein such as vitronectin, collagen and laminine with the corresponding receptor on the surface of various cell species and to particularly suppress the expression of platelet thrombin and accordingly that it can be used for the treatment of thrombosis, apoplexy, cardiac infarction, angina pectoris, osteolytic diseases (particularly osteoporosis), recurrent stricture after angiogenesis, ischemic disease, inflammation, arteriosclerosis and acute renal failure. Particularly, 1-ethyl methylester 4-[[3-[p-(carboxyamidino)phenyl]-2-oxo-5-oxazolidinyl]methyl]-1-piperazineacetate or a pharmaceutically acceptable salt thereof (hereinafter, referred to as "compound A"), especially a 5R substance which is an optical isomer thereof (generic name: gantofiban; hereinafter, referred to as "gantofiban") and, more especially, a citrate of the said 5R substance (gantofiban citrate) has a good activity and is a compound which has now been in a stage of research and development and expected to be provided as a pharmaceutical agent.

However, in the above-mentioned laid-open patent, there is neither disclosure nor suggestion that the compound A including gantofiban citrate has a property by which manufacture of a stable preparation for oral use is made difficult and also about the stabilization of the said preparation for oral administration.

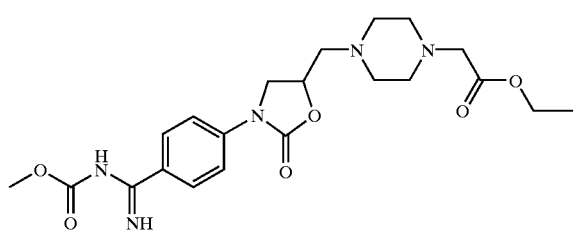

or a pharmaceutically acceptable salt thereof (Compound A)

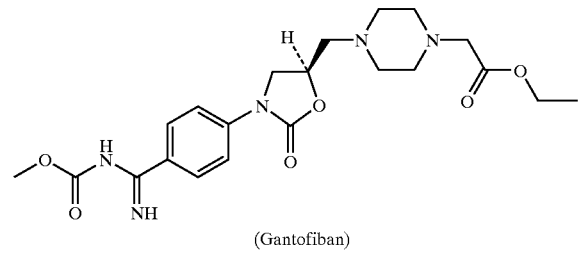

(Gantofiban)

DISCLOSURE OF THE INVENTION

With an object of providing a pharmaceutical agent where the compound A, particularly gantofiban citrate, is an active ingredient, the present inventors have designed a pharmaceutical agent for oral use and have found that, although gantofiban citrate per se is a stable substance, gantofiban citrate is decomposed with a lapse of time in a preparation containing the same. As a result of an intensive study for its cause, it has been found that gantofiban citrate is changed when compounded with fillers, binders and disintegrating agents which are commonly added for oral preparations such as, particularly, lactose, D-mannitol, finely crystalline cellulose, corn starch, calcium hydrogen phosphate, light anhydride silicic acid and cross-carmellose sodium whereupon decomposition with a lapse of time takes place.

Accordingly, an object of the present invention is to provide a stable pharmaceutical composition for oral use comprising the compound A, particularly gantofiban or, more preferably, gantofiban citrate. Another object of the present invention is to provide a method for the manufacture of a stable pharmaceutical composition for oral use comprising the compound A, particularly gantofiban or, more preferably, gantofiban citrate. Still another object of the present invention is to provide a method for the stabilization of a pharmaceutical composition for oral use comprising the compound A, particularly gantofiban or, more preferably, gantofiban citrate.

In view of the above, the present inventors have carried out an intensive investigation for the stabilization of a pharmaceutical composition comprising the compound A and have unexpectedly found that, although coating of the pharmaceutical with an oily base usually results in a retardation of the pharmaceutical because the oily base is hydrophobic and the pharmaceutical is hardly wetted with water, a quick release of the pharmaceutical is not deteriorated giving a stable pharmaceutical composition if an oily base is compounded with the compound A whereupon the present invention has been accomplished.

Thus, the present invention relates to a stable pharmaceutical composition for oral use comprising 1-ethyl methylester 4-[[3-[p-(carboxyamidino)phenyl]-2-oxo-5-oxazolidinyl]methyl]-1-piperazineacetate or a pharmaceutically acceptable salt thereof and an oily base; particularly to the said pharmaceutical composition for oral use in which the oily base is selected one or more from the group consisting of higher saturated fatty acid, ester of fatty acid with alcohol, higher alcohol, phospholipid, sterol or its ester, and hydrocarbon; preferably to the said pharmaceutical composition for oral use in which the oily base is selected one or more from the group consisting of higher saturated fatty acid, ester of fatty acid with alcohol, and higher alcohol; more preferably to the said pharmaceutical composition for oral use in which the compound A is gantofiban in a 5R form or, particularly, a citrate thereof; further to the said pharmaceutical composition for oral use in which 0.001–1000 part(s) by weight of the oily base is/are contained to 1 part by weight of the compound A; and still further to the said pharmaceutical composition for oral use in which the compound A is coated with the oily base. The present invention further relates to a method for the manufacture of a pharmaceutical composition for oral use in which the compound A is compounded with an oily base; particularly to the method for the manufacture of a pharmaceutical composition for oral use in which the compound A is coated with an oily base; particularly to the method for the manufacture of a pharmaceutical composition for oral use in which the oily base is selected one or more from the group consisting of higher saturated fatty acid, ester of fatty acid with alcohol, higher alcohol, phospholipid, sterol or its ester, and hydrocarbon; and preferably to the method for the manufacture of a pharmaceutical composition for oral use in which the compound A is gantofiban in a 5R form or, particularly, a citrate thereof. The present invention furthermore relates to a method for the stabilization of a pharmaceutical composition comprising the compound A in which the compound A is compounded with an oily base; particularly to the method for the stabilization of a pharmaceutical composition comprising the compound A in which the compound A is coated with an oily base; particularly to the method for the stabilization of a pharmaceutical composition comprising a compound A in which the oily base is selected one or more from the group consisting of higher saturated fatty acid, ester of fatty acid with alcohol, higher alcohol, phospholipid, sterol or its ester, and hydrocarbon; and preferably to the method for the stabilization of a pharmaceutical composition comprising a compound A in which the compound A is gantofiban in a 5R form or, particularly, a citrate thereof.

The compound A which is used in the present invention includes a pharmaceutically acceptable salt thereof and, usually, the salt is produced from a pharmaceutically acceptable inorganic or organic acid. With regard to the acid used for producing such a salt, examples of the inorganic acid are sulfuric acid, nitric acid, hydrohalo acid such as hydrochloric acid and hydrobromic acid, phosphoric acid such as orthophosphoric acid and sulfamic acid while examples of the organic acid are aliphatic, alicyclic, aromatic-aliphatic, aromatic or heterocyclic monocarboxylic acids, polycarboxylic acids, sulfonic acids and sulfuric acids. More specific examples of such organic acids are formic acid, acetic acid, trifluoroacetic acid, propionic acid, pivalic acid, diethylacetic acid, malonic acid, succinic acid, pimellic acid, fumaric acid, maleic acid, lactic acid, tartaric acid, malic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalenemonosulfonic acid, naphthalenedisulfonic acid and laurylsulfuric acid.

There is no particular limitation for the oily base which is used in the present invention so far as its pharmaceutical use is usually acceptable and its examples are ester of fatty acidwith alcohol, fat/oil, wax, higher saturated fatty acid, higher alcohol, phospholipid, sterol or its ester and hydrocarbon. It is preferred that the oily base used in the present invention is not melted or dissolved at ambient temperature but is melted upon heating.

The ester of fatty acid with alcohol stands for an ester of the fatty acid with the alcohol as exemplified below. The fatty acid may, for example, be either monocarboxylic acid or dicarboxylic acid. Specific examples of the dicarboxylic acid are oxalic acid, malonic acid, succinic acid, glutaric acid, adipic acid, maleic acid, fumaric acid, phthalic acid, isophthalic acid, terephthalic acid and sebacic acid. Specific examples of the monocarboxylic acid are a straight-chain saturated fatty acid such as acetic acid, propionic acid, butyric acid, valeric acid, caproic acid, heptanoic acid, caprylic acid, nonanoic acid, capric acid, undecanoic acid, lauric acid, tridecanoic acid, myristic acid, pentadecanoic acid, palmitic acid, margaric acid, stearic acid, nonadecanoic acid, arachic acid, heneiconoic acid, behenic acid, tricosanoic acid and lignoceric acid; a straight-chain unsaturated fatty acid such as 10-undecenoic acid, 11-dodecenoic acid, 12-tridecenoic acid, trans-2-tetradecenoic acid, myristoleic acid, trans-9-tetradecenoic acid, 10-pentadecenoic acid, trans-2-hexadecenoic acid, palmitoleic acid, palmitoelaidic acid, 10-heptadecenoic acid, trans-10-heptadecenoic acid, trans-2-octadecenoic acid, petroselinic acid, petroelaidic acid, oleic acid, elaidic acid, cis-vaccenic acid, trans-vaccenic acid, linoleic acid, linoelaidic acid, γ-linolenic acid, a-linolenic acid, 7-nonadecenoic acid, 10-nonadecenoic acid, trans-10-nonadecenoic acid, 10,13-nonadecadienoic acid, trans-10,trans-13-nonadecadienoic acid, 5-icosenoic acid, 8-icosenoicacid, 11-icosenoicacid, trans-11-icosenoicacid, 11,14-icosadienoic acid, 8,11-icosadiynoic acid, meed acid, homo-γ-linolenic acid, 11,14,17-icosatrienoic acid, 5,8,11-icosatriynoic acid, arachidonic acid, icosatetraynoic acid, 5,8,11,14,17-icosapentaenoic acid (EPA), 12-henicosenoic acid, erucic acid, brassidic acid, 13,16-docosadienoic acid, 13,16,19-docosatrienoic acid, 7,10,13,16-docosatetraenoic acid, 7,10,13,16,19-docosapentaenoic acid, 7,10,13,16,19-docosahexaenoic acid (DHA), 14-tricosenoic acid, trans-14-tricosenoic acid and 15-tetracosenoic acid; a branchedfattyacidsuchasisolauricacid, 11-methyldodecanoic acid, isomyristic acid, 13-methyltetradecanoic acid, isopalmiticacid, 15-methylhexadecanoicacid, isostearicacid, 17-methyloctadecanoic acid, isoarachic acid, 19-methylicosanoic acid, 9-methylundecanoic acid, 10-methyldodecanoic acid, 11-methyltridecanoic acid, 12-methyltetradecanoic acid, 13-methylpentadecanoic acid, 14-methylhexadecanoic acid, 15-methylheptadecanoic acid and 16-methyloctadecanoic acid; and a hydroxy fatty acid such as β-hydroxybutanoic acid, γ-hydroxybutanoic acid, 3-hydroxynonanoic acid, 2-hydroxydecanoic acid, 2-hydroxylauric acid, 2-hydroxytetradecanoic acid, 3-hydroxymyristic acid, 2-hydroxyhexadecanoic acid, 2-hydroxyoctadecanoic acid, 12-hydroxystearic acid, 2-hydroxyicosanoic acid, 2-hydroxydocosanoic acid, licinolic acid and licinelaidic acid.

Examples of the alcohol in the ester of fatty acid with alcohol are a straight-chain or branched primary alcohol such as methyl alcohol, ethyl alcohol, n-propyl alcohol, n-butyl alcohol, n-pentyl alcohol, n-hexyl alcohol, n-heptyl alcohol, n-octyl alcohol, n-decyl alcohol, n-lauryl alcohol, n-myristyl alcohol, n-cetyl alcohol, n-octadecyl alcohol, isopropyl alcohol, isobutyl alcohol, sec-butyl alcohol, tert-butyl alcohol, isopentyl alcohol and tert-pentyl alcohol; a secondary alcohol such as ethylene glycol, propylene glycol and 1,3-propanediol; and a tertiary alcohol such as glycerol.

With regard to an ester of the fatty acid with the alcohol as such, any ester which is formed from the above fatty acid with the above alcohol may be used and the ester may be either a natural product or a product obtained by a chemical synthesis. In the case of a natural product, that where other components such as fatty acid and hydrocarbon may be mixed with one or more ester(s) of fatty acid with alcohol as in fat/oil and wax.

Examples of the fat/oil are soybean oil, olive oil, rapeseed oil, peppermint oil, sesame oil, castor oil, tsubaki oil, wheat germ oil, fennel oil, corn oil, sunflower oil, cotton seed oil, coconut oil, peanut oil and a hydrogenated oil thereof. Among them, a hydrogenated oil such as hydrogenated castor oil or hydrogenated rapeseed oil is preferred. Examples of the wax are carnauba wax, whale wax, bees wax and white wax. Examples of the higher saturated fatty acid are caprylic acid, capric acid, myristic acid, palmitic acid, stearic acid and behenic acid. Examples of the higher alcohol are cetyl alcohol and stearyl alcohol. Examples of the phospholipid are hydrogenated lecithin, etc. Examples of the sterol or its ester are cholesterol, α-cholestan, β-cholestanol, epicoprostanol, desmosterol, fucosterol, lanosterol, ergosterol and β-sitosterol. Examples of the hydrocarbon are paraffin and microcrystalline wax.

With regard to the oily base used in the present invention, one kind may be used or more kinds may be used jointly. Among them, higher saturated fatty acid, ester of fatty acid with alcohol, and higher alcohol are preferred.

The pharmaceutical composition of the present invention is that for oral use in which the compound A, particularly gantofiban or, more preferably, gantofiban citrate is stabilized in view of pharmaceutical preparations. The said pharmaceutical composition is used for administration in a solid form such as powder, granules and tablets. Such a solid form can be manufactured by a known method per se. For example, the following methods are available. Thus, when an oily base which is liquid or semi-solid at room temperature (from 5 to 30° C.) is used, the compound A is added thereto and dispersed therein by, for example, means of stirring to give a composition. When an oily base which is solid at room temperature (from 5 to 30° C.) is used, it is made into liquid by a known method per se such as that the oily base is heated at its melting point or higher, the compound A is dispersed therein by, for example, means of dissolving or stirring and the mixture is cooled to solidify whereupon a composition is prepared. In the solidification, it is also possible to mold into particles or pellets if necessary. With regard to such a molding, known methods per se are used. For example, in molding into particles, fine particles having a particle size of preferably about 0.1 to about 1000 μm are prepared. With regard to a molding method, known methods per se are used. They are, for example, a spray chilling method in which a solution or a dispersion of the above compound A in the oily base is quickly chilled and solidified to give fine oil droplets; a method in which a solution or a dispersion of the compound A and the oily base in a solvent is subjected to a spray drying; a method in which a solution or a dispersion of the compound A is dispersed in an aqueous phase; and a spray congealing method. In that case, with regard to an aqueous phase, an aqueous solution containing, if necessary, a dispersing agent (such as Tween 80, carboxymethyl cellulose and polyvinyl alcohol) or the like may be used for avoiding the aggregation of the particles.

Amount of the oily base added thereto in the present invention may be appropriately selected depending upon the physical and chemical properties (such as solubility and dispersibility) of the oily base and the compound A in the composition and on the effective dose or dosage form of the compound A. There is no particular limitation for the adding amount so far as it is usually acceptable in pharmacy and is able to stabilize the compound A but, usually, it is 0.001–1000 part(s) by weight, preferably 0.01–100 part(s) by weight or, more preferably, 0.1–10 part(s) by weight to one part by weight of the compound A. If necessary, it is also possible to further use a preservative (such as benzyl alcohol, ethyl alcohol, benzalkonium chloride, phenol and chlorobutanol), an antioxidant (such as butylhydroxyanisole, propyl gallate, ascorbic acid palmitate, α-tocopherol and DHT), a thickener (such as lecithin, hydroxypropyl cellulose and aluminum stearate), etc.

In the manufacture of the pharmaceutical preparation of the present invention for oral use, an additive which is commonly used for the manufacture of pharmaceutical preparations for oral use may be added for the control of the release of the main ingredient or f or making into the preparation. Examples of such an additive are a filler (such as corn starch, talc, crystalline cellulose, powdery sugar, magnesium stearate, mannitol, light anhydride silicic acid, magnesium carbonate, calcium carbonate and L-cysteine), a binder (such as starch, sucrose, gelatin, gum arabic powder, methyl cellulose, carboxymethyl cellulose, carboxymethyl cellulose sodium, hydroxypropyl cellulose, hydroxypropyl methyl cellulose, polyvinylpyrrolidone, pullulan and dextrin), a disintegrating agent (such as carboxymethyl cellulose calcium and lowly-substituted hydroxy propyl cellulose), an anionic surface-active agent (such as sodium alkyl sulfate), a nonionic surface-active agent (such as polyoxyethylene sorbitan fatty acid ester, polyoxyethylene fatty acid ester and polyoxyethylene castor oil derivative), an antacid or a protecting agent for mucous membrane (such as magnesium hydroxide, magnesium oxide, aluminum hydroxide, aluminum sulfate, magnesium metasilicate aluminate, magnesium silicate aluminate and sucralfate), cyclodextrin and carboxylic acid thereof (such as maltosyl-β-cyclodextrin and maltosyl-β-cyclodextrin carboxylic acid), a coloring agent, a corrigent, an adsorbent, an antiseptic agent, a moisturizer, an anticharging agent and an elongating agent for disintegration. Adding amount of the above additive may be appropriately selected within such an extent that stability and absorbing ability of the main ingredient and adding effect of the oily base are not deteriorated.

When the pharmaceutical composition of the present invention for oral use is made into a powdery preparation, it is also possible to manufacture the preparation from a pharmaceutical composition in a solid form. Thus, in the manufacture of a powdery preparation, the above-mentioned pharmaceutical composition in a solid form is homogeneously mixed with the above-mentioned additive or is granulated using an appropriate solvent such as water whereby the preparation can be manufactured. In the granulation, common granulating machines such as a tumbling granulator, a stirring granulator, a fluididizing granulator, a centrifugally tumbling granulator and a tumbling/fluidizing granulator, compressing granulators such as a roller compactor or machines of a tumbling and tightly compressing type are used. In the case of mixing, the above-mentioned granulators may be used or common mixers such as mixers of a rotary cylinder type, a double cone type, a V-shaped type, a ribbon type and a screw type may be used. The mixed powder or the granulated powder prepared as such is filled in capsules whereupon a hard capsule preparation can be manufactured. With regard to the capsules in that case, hard capsules made of gelatin having an inner volume of from about 0.13 to 1.37 ml are generally used and filling is carried out by means of a filling machine of a disc type, a compress type or an Auger type. It is also possible to make the pharmaceutical composition of the present invention into tablets by means of tabletting of the above-prepared mixed powder or granulated powder. Shape and size of the tablet may be appropriately selected and, for example, the tablets may be prepared in a shape of ellipse, football or heart or may have a score for dividing. With regard to a tabletting machine, any of that of an eccentric type or a rotary type may be used for preparing the tablets.

The pharmaceutical composition of the present invention may be made into an enteric preparation by coating with an enteric coating agent. An enteric coating agent as such is an enteric polymer which is substantially insoluble in an acidic region but is at least partially soluble in a weakly acidic to a basic region. Here, the acidic region means the pH of from about 0.5 to about 4.5 or, preferably, from about 1.0 to about 2.0 while the weakly acidic to the basic region means the pH of from about 5.0 to 9.0 or, preferably, from about 6.0 to about 7.5. To be more specific, cellulose acetate phthalate, hydroxypropyl methyl cellulose, hydroxypropyl methyl cellulose phthalate, hydroxypropyl methyl acetate succinate (manufactured by Shin-Etsu Chemical) and methacrylate copolymer (manufactured by Röhm GmbH; trade name: Eudragit L 30D55, L 100-55, L 100, S 100, etc.) may be exemplified. Even when those agents per se are used as enteric preparations, the products are still effective in terms of safety, etc.

With regard to a coating method, common methods such as a pan coating, a fluidizing coating and a tumbling coating may be adopted. When a coating agent is a solution or a dispersion containing water or an organic solvent, a spray coating method may be adopted as well. There is no particular limitation for the ratio of water or the organic solvent used for the manufacture of a coating agent but any ratio may be used. There is no particular limitation for the type of the organic solvent and, for example, alcohol (such as methanol, ethanol and isopropyl alcohol), ketone (such as acetone) and halogenated hydrocarbon (such as chloroform, dichloromethane and trichloromethane) may be used. It is also effective in terms of safety, etc. that the pharmaceutical composition of the present invention is filled in capsules which are coated with the above-mentioned enteric coating agent and used as enteric capsules. With regard to the capsule, gelatin capsule, etc. may be used for example.

The pharmaceutical composition of the present invention may be safely administered to mammals (such as mouse, rat, hamster, rabbit, cat, dog, cattle, horse, sheep, monkey and human being) keeping the good pharmacological action of the compound A. To be more specific, the compound A used in the present invention is able to suppress the interaction of integrin receptor with a ligand, to particularly suppress a binding of fibrinogen, fibronectin and a von Willebrand factor with fibrinogen receptor (glycoprotein IIb/IIIa) of platelets, to suppress a binding of adhesion protein such as vitronectin, collagen and laminine with the corresponding receptor on the surface of various cell species and to particularly suppress the expression of platelet thrombin whereby it can be safely used for the treatment of thrombosis, apoplexy, cardiac infarction, angina pectoris, osteolytic diseases (particularly osteoporosis), recurrent stricture after angiogenesis, ischemic disease, inflammation, arteriosclerosis and acute renal failure and is particularly useful as an inhibitor to platelet aggregation. In addition, the pharmaceutical composition of the present invention may contain other pharmaceutical ingredient as an active ingredient than the compound A where there is no particular limitation for the said other ingredient so far as the object of the present invention can be achieved and the said ingredient can be appropriately used in a suitable ratio.

In the pharmaceutical composition of the present invention, decrease of safety caused by incompatibility can be suppressed or prevented even during storage or preservation and, moreover, decrease of the pharmacological activity of the compound A during the process for manufacturing the preparation can be suppressed. Accordingly, in the pharmaceutical preparation of the present invention, a sufficiently controlled activity of the compound A can be maintained during a usual storage period and surer therapeutic effect can be expected.

BEST MODE FOR CARRYING OUT THE INVENTION

The present invention will now be more specifically illustrated by way of the following Examples and Comparative Examples although the present invention is not limited thereto.

EXAMPLE 1

One part by weight of gantofiban citrate and 5 parts by weight of hydrogenated oil (K3 Wax; manufactured by Kawaken Fine Chemical) were mixed using a mortar and sieved through a sieve of 32 mesh, 94 parts by weight of partly pregelatinized starch (PCS; manufactured by Asahi Chemical Industry) were added followed by mixing and the mixture was sieved through a sieve of 32 mesh to prepare a diluted powder preparation.

EXAMPLE 2

Stearic acid (5 parts by weight) was taken in a vessel and heated to melt on a hot water bath, 1 part by weight of gantofiban citrate was added and the mixture was stirred to disperse. The melted dispersion was spray-solidified using a spray drier (type L-8; manufactured by Ogawara Seisakusho; disk diameter: 50 mm; rotating speed: 30,000 rpm) and sieved through a sieve of 42 mesh to prepare fine microparticles. To 6 parts of the fine microparticles were added 94 parts by weight of a partly pregelatinized starch (PCS; manufactured by Asahi Chemical Industry) followed by mixing and the mixture was sieved through a sieve of 32 mesh to give a diluted powder preparation.

EXAMPLE 3

Stearic acid (5 parts by weight) was taken in a vessel and heated to melt on a hot water bath, 1 part by weight of gantofiban citrate was added and the mixture was stirred to disperse. The melted dispersion was spray-solidified using a spray drier (type L-8; manufactured by Ogawara Seisakusho; disk diameter: 50 mm; rotating spoeed: 30,000 rpm) and sieved through a sieve of 42 mesh to prepare fine microparticles. To 6 parts of the fine microparticles were added 94 parts by weight of D-mannitol (manufactured by Towa Kasei Kogyo) followed by mixing and the mixture was sieved through a sieve of 32 mesh to give a diluted powder preparation. For comparison, 1 part by weight of gantofiban citrate and 99 parts by weight of D-mannitol (manufactured by Towa Kasei Kogyo) were mixed in a mortar and sieved through a sieve of 32 mesh to prepare a diluted powder preparation which was used as a control. Each of those samples was placed in a plastic bottle and stored in an open state at 40° C. and 75% relative humidity and the stability during one month was compared. Result of comparison of the stability is as shown in the following Table 1. Incidentally, with regard to the stability, free 1-ethyl methylester 4-[[(5R)-3-[p-(carboxyamidino)phenyl]-2-oxo-5-oxazolidinyl]methyl]-1-piperazineacetate which was an active ingredient was determined by means of a high performance liquid chromatography and the residual value (%) was calculated from the amounts of the effective ingredient before initiation of the storage test and after the completion of the storage test.

TABLE 1

| Period | Residual value (%) | |
| --- | --- | --- |
| | The Present Invention | Control |
| Initial Value | 100 | 100 |
| After One Month | 101.0 | 89.4 |

Result and Discussion

In the control preparation, decrease of the residual value was noted while, in the preparation (diluted powder preparation) of the present invention, no decrease of the residual value was noted. This is supposed to be due to the fact that gantofiban citrate was coated with stearyl alcohol (an oily base) whereby its contact with D-mannitol resulting in incompatibility was suppressed.

EXAMPLE 4

Stearic acid (5 parts by weight) was taken in a vessel and heated to melt on a hot water bath, 1 part by weight of gantofiban citrate was added and the mixture was stirred to disperse. The melted dispersion was spray-solidified using a spray drier (type L-8; manufactured by Ogawara Seisakusho; disk diameter: 50 mm; rotating speed: 30,000 rpm) and sieved through a sieve of 42 mesh to prepare fine microparticles. To 6 parts of the fine microparticles were added 73.5 parts by weight of lactose (Dilactose S), 20 parts by weight of a partly pregelatinized starch (PCS; manufactured by Asahi Chemical Industry) and 0.5 part by weight of magnesium stearate followed by mixing and the mixture was compressed using a rotary tabletting machine (manufactured by Hata Tekkosho; HT-P-22) to give tablets. For comparison, 1 part by weight of gantofiban citrate, 78.5 parts by weight of lactose (Dilactose S; manufactured by Freund Sangyo), 20 parts by weight of partly pregelatinized starch (PCS; manufactured by Asahi Chemical Industry) and 0.5 part by weight of magnesium stearate were mixed and the mixture was compressed using a rotary tabletting machine (manufacturedbyHataTekkosho; HT-P-22) togivetablets which were used as a control. Each of those samples was placed in a plastic bottle and stored in an open state at 40° C. and 75% relative humidity for one month and the stability was compared. Result of comparison of the stability (decomposing rate) is as shown in the following Table 2.

TABLE 2

| Period | Residual value (%) | |
| --- | --- | --- |
| | The Present Invention | Control |
| Initial Value | 100 | 100 |
| After One Month | 93.5 | 78.4 |

Result and Discussion

In the control preparation, a significant decrease of the residual value was noted while, in the preparation (tablets) of the present invention, decrease of the residual value was suppressed as compared with the control preparation. This is supposed to be due to the fact that gantofiban citrate was coated with stearic acid (an oily base) whereby its contacting area with the fillers decreased.

Industrial Applicability

In accordance with the present invention, 1-ethyl methylester 4-[[3-[p-(carboxyamidino)phenyl]-2-oxo-5-oxazolidinyl]methyl]-1-piperazineacetate or a pharmaceutically acceptable salt thereof having an antagonistic action to GPIIb/IIIa receptor is mixed or coated with an oily base whereby a stabilized pharmaceutical composition can be manufactured and it is possible to provide a pharmaceutical composition which is durable for storage of longer period.

What is claimed is:

1. A pharmaceutical composition for oral use comprising
   (A) 1-ethyl methylester 4-[[3-[p-(carboxyamidino)phenyl]-2-oxo-5-oxazolidinyl]methyl]-1-piperazineacetate or a pharmaceutically acceptable salt thereof; and
   (B) an oily base, comprising one or more members selected from the group consisting of a higher saturated fatty acid, an ester of a fatty acid with an alcohol, a higher alcohol, and a hydrocarbon.

2. The pharmaceutical composition according to claim 1, wherein 1-ethyl methylester 4-[[3-[p-(carboxyamidino)phenyl]-2-oxo-5-oxazolidinyl]methyl]-1-piperazineacetate or a pharmaceutically acceptable salt thereof is coated with said oily base.

3. The pharmaceutical composition according to claim 2, wherein the higher saturated fatty acid is stearic acid; the ester of fatty acid with alcohol is hydrogenated oil; the higher alcohol is stearyl alcohol; and the hydrocarbon is at least one of paraffin and microcrystalline wax.

4. The pharmaceutical composition according claim 2, wherein 0.001–1000 part(s) by weight of the oily base are present in said composition per 1 part by weight of 1-ethyl methylester 4-[[3-[p-(carboxyamidino)phenyl]-2-oxo-5-oxazolidinyl]methyl]-1-piperazineacetate or a pharmaceutically acceptable salt thereof.

5. The pharmaceutical composition according to claim 4, wherein 1-ethyl methylester 4-[[3-[p-(carboxyamidino)phenyl]-2-oxo-5-oxazolidinyl]methyl]-1-piperazineacetate or a pharmaceutically acceptable salt thereof is a 5R isomer.

6. The pharmaceutical composition according to claim 5, wherein 1-ethyl methylester 4-[[3-[p-(carboxyamidino)phenyl]-2-oxo-5-oxazolidinyl]methyl]-1-piperazineacetate or a pharmaceutically acceptable salt thereof is a citrate of the 5R isomer.

7. A method of manufacturing a pharmaceutical composition for oral use, which comprises compounding (A) 1-ethyl methylester 4-[[3-[p-(carboxyamidino)phenyl]-2-oxo-5-oxazolidinyl]methyl]-1-piperazineacetate or a pharmaceutically acceptable salt thereof; with (B) an oily base comprising one or more members selected from the group consisting of a higher saturated fatty acid, an ester of a fatty acid with alcohol, a higher alcohol, and a hydrocarbon.

8. The method according to claim 7, wherein 1-ethyl methylester 4-[[3-[p-(carboxyamidino)phenyl]-2-oxo-5-oxazolidinyl]methyl]-1-piperazineacetate or a pharmaceutically acceptable salt thereof is coated with said oily base.

9. The method according to claim 7, wherein the higher saturated fatty acid is stearic acid; the ester of fatty acid with alcohol is hydrogenated oil; the higher alcohol is stearyl alcohol; and the hydrocarbon is at least one of paraffin and microcrystalline wax.

10. The method according to claim 7, wherein 1-ethyl methylester 4-[[3-[p-(carboxyamidino)phenyl]-2-oxo-5-oxazolidinyl]methyl]-1-piperazineacetate or a pharmaceutically acceptable salt thereof is a 5R isomer.

11. The method of manufacturing a pharmaceutical composition for oral use according to claim 10, wherein 1-ethyl methylester 4-[[3-[p-(carboxyamidino)phenyl]-2-oxo-5-oxazolidinyl]methyl]-1-piperazineacetate or a pharmaceutically acceptable salt thereof is a citrate of the 5R isomer.

12. A method for stabilizing a pharmaceutical composition for oral use which comprises compounding (A) 1-ethyl methylester 4-[[3-[p-(carboxyamidino)phenyl]-2-oxo-5-oxazolidinyl]methyl]-1-piperazineacetate or a pharmaceutically acceptable salt thereof; with (B) an oily base, comprising one or more members selected from the group consisting of a higher saturated fatty acid, an ester of a fatty acid with alcohol, a higher alcohol, and a hydrocarbon.

13. The method according to claim 12, wherein 1-ethyl methylester 4-[[3-[p-(carboxyamidino)phenyl]-2-oxo-5-oxazolidinyl]methyl]-1-piperazineacetate or a pharmaceutically acceptable salt thereof is coated with said oily base.

14. The method according to claim 12, wherein the higher saturated fatty acid is stearic acid; the ester of fatty acid with alcohol is hydrogenated oil; the higher alcohol is stearyl alcohol; and the hydrocarbon is at least one of paraffin and microcrystalline wax.

15. The method according to claim 12, wherein 1-ethyl methylester 4-[[3-[p-(carboxyamidino)phenyl]-2-oxo-5-oxazolidinyl]methyl]-1-piperazineacetate or a pharmaceutically acceptable salt thereof is a 5R isomer.

16. The method for stabilizing a pharmaceutical composition for oral use according to claim 15, wherein 1-ethyl methylester 4-[[3-[p-(carboxyamidino)phenyl]-2-oxo-5-oxazolidinyl]methyl]-1-piperazineacetate or a pharmaceutically acceptable salt thereof is a citrate of the 5R isomer.

* * * * *